(12) United States Patent
Hurson

(10) Patent No.: US 7,806,693 B2
(45) Date of Patent: Oct. 5, 2010

(54) DENTAL IMPLANT

(75) Inventor: Steve Hurson, Yorba Linda, CA (US)

(73) Assignee: Nobel Biocare Services AG, Zurich-Flughafen (CH)

( * ) Notice: Subject to any disclaimer, the term of this patent is extended or adjusted under 35 U.S.C. 154(b) by 244 days.

(21) Appl. No.: 11/739,034

(22) Filed: Apr. 23, 2007

(65) Prior Publication Data

US 2008/0261175 A1 Oct. 23, 2008

(51) Int. Cl.
*A61C 8/00* (2006.01)
(52) U.S. Cl. ..................................... 433/174
(58) Field of Classification Search .............. 433/102, 433/172–176; 411/16, 386, 393, 394, 411, 411/412, 414, 416, 421, 423, 424, 426
See application file for complete search history.

(56) References Cited

U.S. PATENT DOCUMENTS

| | | |
|---|---|---|
| 1,698,951 A | 1/1929 | Holmes |
| 2,215,770 A | 9/1940 | Sheffield |
| 3,672,058 A | 6/1972 | Nikoghossian |
| 3,797,113 A | 3/1974 | Brainin |
| 3,849,887 A | 11/1974 | Brainin |
| 4,103,422 A | 8/1978 | Weiss et al. |
| 4,406,623 A | 9/1983 | Grafelmann et al. |
| 4,431,416 A | 2/1984 | Niznick |
| 4,468,200 A | 8/1984 | Munch |
| 4,547,157 A | 10/1985 | Driskell |
| 4,645,453 A | 2/1987 | Niznick |
| 4,713,003 A | 12/1987 | Symington et al. |
| 4,738,623 A | 4/1988 | Driskell |
| 4,758,161 A | 7/1988 | Niznick |
| 4,826,434 A | 5/1989 | Krueger |
| 4,863,383 A | 9/1989 | Grafelmann |
| 4,932,868 A | 6/1990 | Linkow et al. |
| 4,960,381 A | 10/1990 | Niznick |
| 4,976,739 A | 12/1990 | Duthie, Jr. |
| 5,000,686 A | 3/1991 | Lazzara et al. |

(Continued)

FOREIGN PATENT DOCUMENTS

DE 10231743 2/2004

(Continued)

OTHER PUBLICATIONS

English translation of WO 2005/117742 to Neumeyer, Dec. 15, 2005.*

(Continued)

*Primary Examiner*—Cris L Rodriguez
*Assistant Examiner*—Michael R Ballinger
(74) *Attorney, Agent, or Firm*—Knobbe, Martens, Olson & Bear LLP

(57) ABSTRACT

A dental implant is provided for supporting a dental prosthesis. The implant can comprise a body having an outer surface, a distal end, and a proximal end. The dental implant can include at least one thread located on at least a portion of the outer surface of the body. The thread can include a proximal flank and a distal flank. The thread can also include a face that extends between the proximal flank and the distal flank. Further, the dental implant can include a first helical groove formed on the face and/or a second helical groove formed on the body.

18 Claims, 11 Drawing Sheets

U.S. PATENT DOCUMENTS

| | | | |
|---|---|---|---|
| 5,007,835 A | 4/1991 | Valen |
| 5,061,181 A | 10/1991 | Niznick |
| 5,062,800 A | 11/1991 | Niznick |
| 5,071,350 A | 12/1991 | Niznick |
| 5,074,790 A | 12/1991 | Bauer |
| 5,076,788 A | 12/1991 | Niznick |
| RE33,796 E | 1/1992 | Niznick |
| 5,078,607 A | 1/1992 | Niznick |
| 5,087,201 A | 2/1992 | Mondani et al. |
| 5,195,892 A | 3/1993 | Gersberg |
| 5,226,766 A | 7/1993 | Lasner |
| 5,230,590 A | 7/1993 | Bohannan et al. |
| 5,328,371 A | 7/1994 | Hund et al. |
| 5,343,391 A | 8/1994 | Mushabac |
| 5,427,527 A | 6/1995 | Niznick et al. |
| 5,433,606 A | 7/1995 | Niznick |
| 5,435,723 A | 7/1995 | O'Brien |
| 5,439,381 A | 8/1995 | Cohen |
| 5,484,286 A | 1/1996 | Hansson |
| 5,527,183 A | 6/1996 | O'Brien |
| 5,571,017 A | 11/1996 | Niznick |
| 5,580,246 A | 12/1996 | Fried et al. |
| 5,584,629 A | 12/1996 | Bailey et al. |
| 5,601,429 A | 2/1997 | Blacklock |
| 5,628,630 A | 5/1997 | Misch et al. |
| 5,639,237 A | 6/1997 | Fontenot |
| 5,642,996 A | 7/1997 | Mochida et al. |
| 5,674,072 A | 10/1997 | Moser et al. |
| 5,725,375 A | 3/1998 | Rogers |
| 5,782,918 A | 7/1998 | Klardie et al. |
| 5,795,160 A | 8/1998 | Hahn et al. |
| 5,810,590 A | 9/1998 | Fried et al. |
| 5,816,812 A | 10/1998 | Kownacki et al. |
| 5,823,776 A | 10/1998 | Duerr et al. |
| 5,823,777 A | 10/1998 | Misch et al. |
| 5,871,356 A | 2/1999 | Guedj |
| 5,876,453 A | 3/1999 | Beaty |
| 5,897,319 A | 4/1999 | Wagner et al. |
| 5,915,968 A | 6/1999 | Kirsch et al. |
| 5,938,444 A | 8/1999 | Hansson et al. |
| 5,967,783 A | 10/1999 | Ura |
| 6,095,817 A | 8/2000 | Wagner et al. |
| 6,116,904 A | 9/2000 | Kirsch et al. |
| 6,129,730 A | 10/2000 | Bono et al. |
| 6,135,772 A | 10/2000 | Jones |
| 6,149,432 A | 11/2000 | Shaw et al. |
| 6,200,345 B1 | 3/2001 | Morgan |
| 6,227,859 B1 | 5/2001 | Sutter |
| 6,273,722 B1 | 8/2001 | Phillips |
| 6,287,117 B1 | 9/2001 | Niznick |
| 6,312,259 B1 | 11/2001 | Kvarnstrom et al. |
| 6,315,564 B1 | 11/2001 | Levisman |
| 6,394,806 B1 | 5/2002 | Kumar |
| 6,402,515 B1 | 6/2002 | Palti |
| 6,419,491 B1 | 7/2002 | Ricci et al. |
| 6,481,760 B1 | 11/2002 | Noel et al. |
| 6,626,671 B2 | 9/2003 | Klardie et al. |
| 6,655,962 B1 | 12/2003 | Kennard |
| 6,679,701 B1 | 1/2004 | Blacklock |
| 6,726,689 B2 | 4/2004 | Jackson |
| 6,733,291 B1 | 5/2004 | Hurson |
| 6,733,503 B2 | 5/2004 | Layrolle et al. |
| 6,769,913 B2 | 8/2004 | Hurson |
| 6,913,465 B2 | 7/2005 | Howlett et al. |
| 6,955,258 B2 | 10/2005 | Howlett et al. |
| 7,014,464 B2 | 3/2006 | Niznick |
| 7,108,510 B2 | 9/2006 | Niznick |
| 7,249,949 B2 | 7/2007 | Carter |
| 7,273,373 B2 | 9/2007 | Horiuchi |
| 7,281,925 B2 | 10/2007 | Hall |
| 7,383,163 B2 | 6/2008 | Holberg |
| 2002/0102518 A1 | 8/2002 | Mena |
| 2002/0106612 A1 | 8/2002 | Back et al. |
| 2002/0177106 A1 | 11/2002 | May et al. |
| 2005/0147942 A1 | 7/2005 | Hall |
| 2005/0214714 A1 | 9/2005 | Wohrle |
| 2005/0260540 A1 | 11/2005 | Hall |
| 2005/0287497 A1 | 12/2005 | Carter |
| 2006/0172257 A1 | 8/2006 | Niznick |
| 2006/0183078 A1 | 8/2006 | Niznick |
| 2007/0099153 A1* | 5/2007 | Fromovich ............... 433/174 |
| 2008/0014556 A1* | 1/2008 | Neumeyer ............... 433/174 |
| 2008/0032264 A1 | 2/2008 | Hall |
| 2008/0261176 A1 | 10/2008 | Hurson |
| 2009/0305192 A1 | 12/2009 | Hall |

FOREIGN PATENT DOCUMENTS

| | | |
|---|---|---|
| DE | 10231 743 B4 | 3/2005 |
| EP | 0475358 | 3/1992 |
| EP | 0 707 835 B1 | 10/1995 |
| EP | 0 707 835 | 4/1996 |
| EP | 1 396 236 A | 3/2004 |
| EP | 1624826 A1 | 2/2006 |
| EP | 1 728 486 A | 12/2006 |
| EP | 1624826 A4 | 5/2007 |
| FR | 2 600 246 | 12/1987 |
| JP | 8-501962 | 3/1996 |
| JP | 3026125 | 4/1996 |
| JP | 10-052445 | 2/1998 |
| WO | WO 94/07428 | 4/1994 |
| WO | WO 94/09717 | 5/1994 |
| WO | WO 95/09583 | 4/1995 |
| WO | WO 97/05238 | 2/1997 |
| WO | WO 99/23971 | 5/1999 |
| WO | WO 00/00103 | 1/2000 |
| WO | WO 00/72775 | 12/2000 |
| WO | WO 00/72777 | 12/2000 |
| WO | WO 01/74412 | 10/2001 |
| WO | WO 01/76653 | 10/2001 |
| WO | WO 03/030767 A | 4/2003 |
| WO | WO 03/034951 | 5/2003 |
| WO | WO 03/055405 | 7/2003 |
| WO | WO 03/055406 A1 | 7/2003 |
| WO | WO 03/063085 | 7/2003 |
| WO | WO2004/103202 * | 12/2004 |
| WO | WO2005/117742 * | 12/2005 |

OTHER PUBLICATIONS

Niznick, Gerald A., DMD, MSD. "Proactive Nobel Active New Presentation," Implant Direct™, Oct. 16, 2007.

3.8D series Threaded Implant, dental implant sold before Sep. 27, 1999, Nobel Biocare.

International Preliminary Report on Patentability for PCT Application No. PCT/IL2004/000438 filed May 23, 2004. Publication No. WO 04/103202 A1 published Dec. 2, 2004.

European Search Report for Application No. EP04734484 filed May 23, 2004. Publication No. EP 1624826 A1, published Feb. 15, 2006.

Supplementary European Search Report for Application No. EP04734484 filed May 23, 2004. Publication No. EP 1624826 A4, published May 30, 2007.

Mar. 11, 2004 International Search Report, Application No. PCT/SE 2003/001973, 3 pages.

* cited by examiner

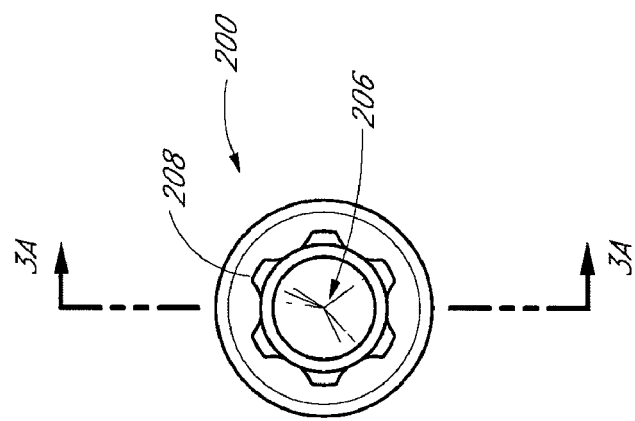
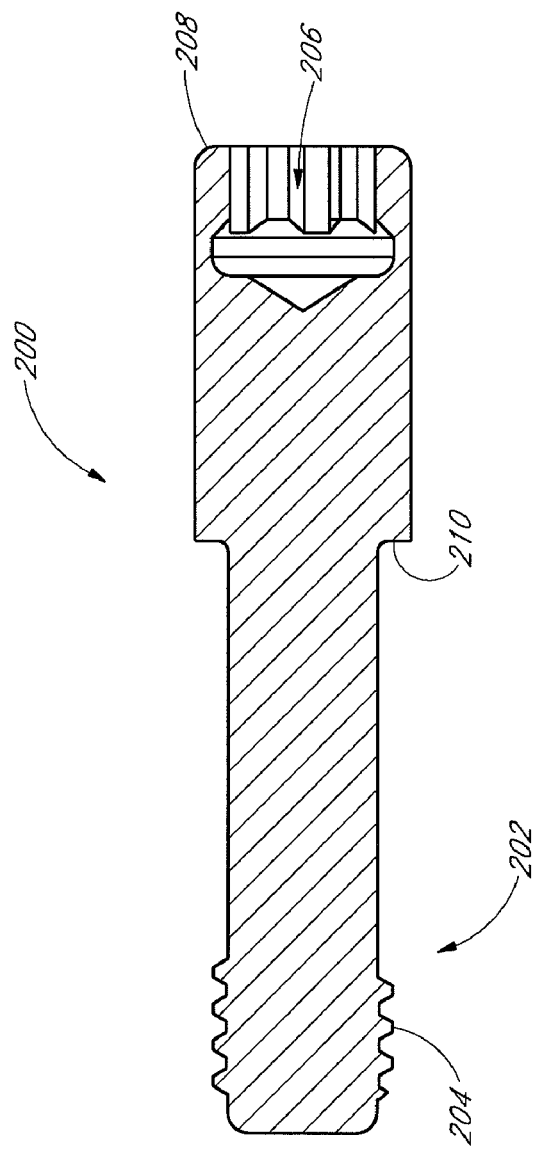
FIG. 3B
FIG. 3A

DENTAL IMPLANT

BACKGROUND

1. Field of the Inventions

The present inventions generally relate to dental implants, and more specifically, to threaded dental implants.

2. Description of the Related Art

Implant dentistry involves the restoration of one or more teeth in a patient's mouth using artificial components. Such artificial components typically include a dental implant and a prosthetic tooth and/or an abutment that is secured to the dental implant. Generally, the process for restoring a tooth is carried out in three stages.

The dental implant is typically fabricated from pure titanium or a titanium alloy. The dental implant typically includes a body portion and a collar. The body portion is configured to extend into and osseointegrate with the alveolar bone. The top surface of the collar typically lies flush with the crest of the jawbone bone. The abutment (e.g., a final abutment) typically lies on the top surface and extends through the soft tissue, which lies above the alveolar bone. Recently, some dental implants have collars that extend above the crest of the jawbone and through the soft tissue.

Implants of various tapers and with various thread profiles are known in the art. For example, U.S. Pat. No. 5,427,527 describes a conical implant design that is placed into a cylindrical osteotomy site in order to induce bone compression at the coronal aspect of the implant, i.e. at its widest end. Other thread profiles and patterns are known in the art. The most common design involves a symmetrical, V-shaped appearance such as that illustrated in U.S. Pat. No. 5,897,319. A variable thread profile is disclosed in U.S. Pat. Nos. 5,435,723 and 5,527,183 which is mathematically optimized for stress transfer under occlusal loads. U.S. Pat. Nos. 3,797,113 and 3,849,887 describe dental implants with external thread-like features having a flat shelf facing the coronal end of the implant.

While such prior art dental implants have been successful, there is a continuing desire to improve a dental implant's ability to osseointegrate with the alveolar bone and to improve the stability of the dental implant within the alveolar bone.

SUMMARY OF THE INVENTION

An embodiment disclosed herein is a dental implant for supporting a dental prosthesis comprising a body. The body can comprise an outer surface, a distal end, and a proximal end. The dental implant can also include at least one thread located on at least a portion of the outer surface of the body. The thread can include a proximal flank and a distal flank. The thread can also include a face that extends between the proximal flank and the distal flank. The dental implant can also include a first helical groove formed on the face and a second helical groove formed on the body.

Another embodiment is a dental implant for supporting a dental prosthesis comprising a body. The body can comprise an outer surface, a distal body portion, and a proximal body portion. The dental implant can also include at least one thread. The thread can comprise a distal thread portion extending over the distal body portion and a proximal thread portion extending over the proximal body portion. The thread can comprise a proximal flank and a distal flank. The thread can further comprise a face extending between the proximal flank and the distal flank wherein the face increases in thickness from the distal thread portion to the proximal thread portion. The dental implant can also include a groove located on the face of at least a portion of the proximal thread portion.

Further embodiments of the invention are defined by the dependent claims. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 3A is a side view of an embodiment of a coupling bolt, which is configured to meet with the implant of FIG. 1A and the abutment of FIG. 2A.

FIG. 3B is a top view of the coupling bolt of FIG. 3A.

DETAILED DESCRIPTION OF THE PREFERRED EMBODIMENTS

Figure 1A:
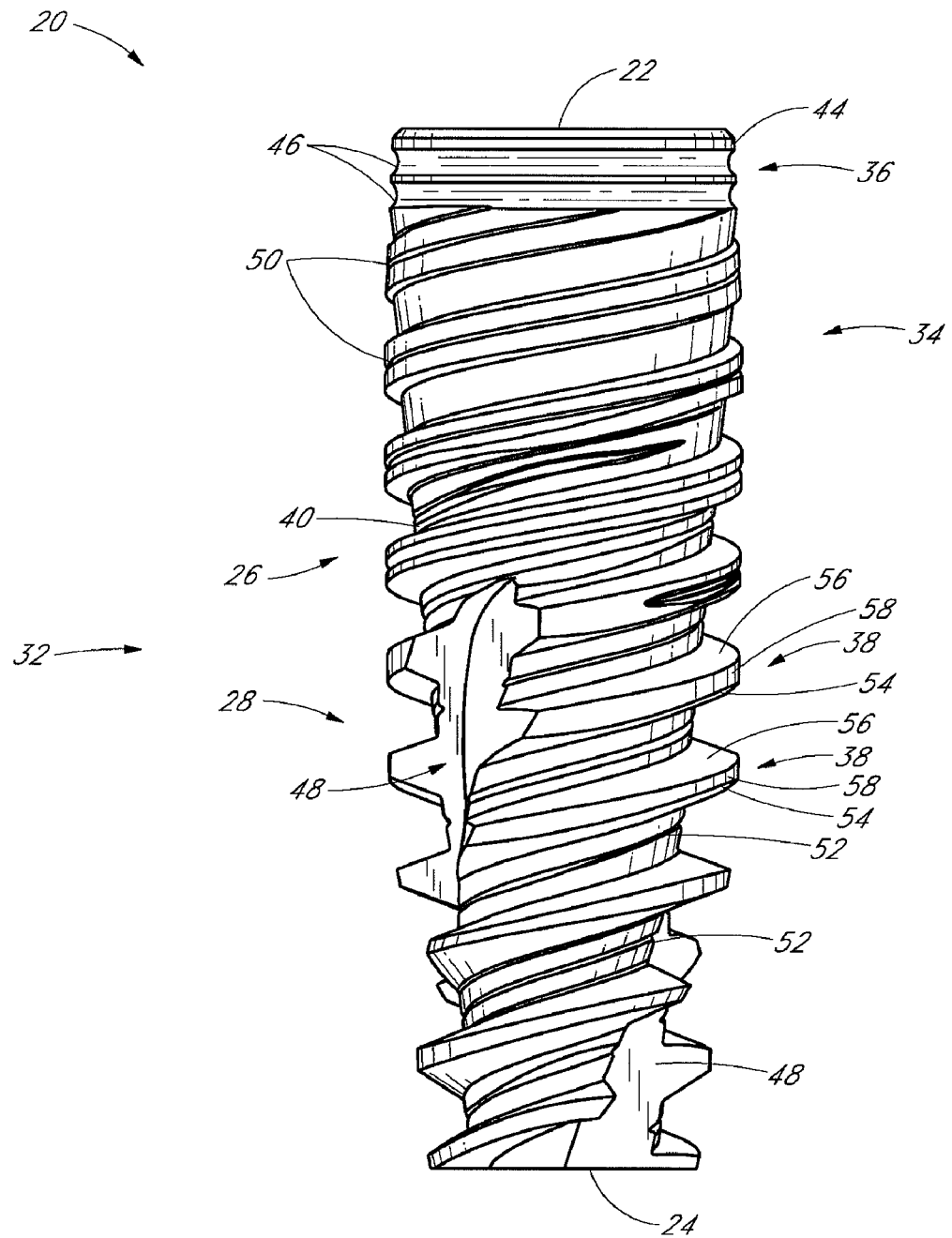
FIG. 1A is a side view of a dental implant in accordance with an embodiment of the present inventions.

FIGS. 1A-1D illustrate an embodiment of a dental implant 20. In this embodiment, the implant 20 comprises an implant body 32, which includes a lower portion 34 and a collar 36. The implant 20 may be made of titanium, although other materials may be used, such as various types of ceramics. The lower portion 34 can be tapered and can include a pair of threads 38 that are located on an outer surface 35 of the lower portion 34. As will be explained below, although the illustrated embodiment includes a pair of threads 38 that each extends helically around the implant, modified embodiments may include more or less threads. In addition, as explained below, the body 32 is illustrated as being generally conical or tapered. However, in other embodiments, the body 32 can be substantially cylindrical or otherwise shaped. The dental implant 20 can comprise a proximal end 22, a proximal portion 26 generally adjacent the proximal end 22, a distal end 24 and a distal portion 28 generally adjacent the distal end.

In the illustrated embodiment, the implant body 32 includes an outer surface or a bone apposition surface 40, which can be configured to promote osseointegration. In one embodiment, the bone apposition surface 40 is configured to promote osseointegration by increasing the surface area of the body 32. In this regard, the bone apposition surface 40 can be formed by roughening the implant body 32 in several different manners, such as, for example, by acid-etching, grit blasting, and/or machining. Alternatively, the bone apposition surface 40 can be formed by coating the lower surface with a substance in order to promote osseointegration. In some embodiments, this may result in decreasing or increasing the surface area of the implant body 32. Calcium phosphate ceramics, such as tricalcium phosphate (TCP) and hydroxyapatite (HA) are examples of materials that can enhance osseointegration by changing the chemistry of the outer surface 40. In other embodiments, the outer surface 28 can comprise macroscopic structures, such as, for example, threads, micro-threads, indentations, and/or grooves that are configured to promote osseointegration and can be used alone or combined with the roughening and/or the coatings described above. In one embodiment, the outer surface 28 comprises a microstructure surface, such as, a highly crystalline and phosphate enriched titanium oxide microstructured surface with open pores in the low micrometer range. An example of such a surface is sold under the trademark, TiUnite™ by Nobel Biocare AB™. In another embodiment, it is particularly advantageous for a zirconium ceramic body can be coated with porous zirconium to provide a microstructure surface. In another embodiment, the microstructure surface can be coated with a substance configured to promote osseointegration (such as BMP).

With continued reference to FIG. 1A, the collar 36 can lie above the lower portion 34 and, in the illustrated embodiment, can be integrally formed with or permanently affixed to the lower portion 34. The collar 36 can be defined at least in part by a sidewall 44. In the illustrated embodiment, the sidewall 44 includes two semicircular grooves 46 that are positioned circumferentially around the sidewall 44 of the collar 36. The semicircular grooves 46 can provide additional growth surface for soft tissue, such as that of a patient's gums. In one embodiment, the semi-circular grooves 46 have a width of about 150 microns and a depth of about 50 microns. The grooves 46 can be sized so that one or more grooves 46 occupy a substantial portion of the collar 36. In the illustrated embodiment of FIG. 1A, two grooves 46 are shown as occupying a substantial portion of the collar 36 (e.g., greater than 50% of a total area). In modified embodiments, the collar 36 can be provided with more, less or no grooves and/or grooves with different dimensions and configurations. In other embodiments, the circumferential protrusions or microthreads can be provided on the collar 36. In general, such structures on the collar 36 are advantageously configured to load the harder cortical bone through which the implant 20 is inserted but to a lesser extent as compared to the threads 38 of the implant 20, which can be configured to engage the spongy cancellous bone positioned below the cortical bone. In other embodiments, the collar 36 can be non-cylindrical with, for example, inwardly tapered or have a reverse taper side wall.

In the embodiment shown in FIGS. 1A-1D, each of the threads 38 comprises a distal flank 54 and a proximal flank 56 that are connected by a face 58. As mentioned above the illustrated dental implant 20 includes a pair of threads 38 that begin at opposing sides of the distal end 24 and progress towards the proximal end 22 along the lower portion 34 while maintaining opposing positions along the lower portion 34 of the implant body 32. Accordingly, in the illustrated embodiment each of the threads 38 have the same pitch. It will be appreciated that, although the illustrated embodiment shows two threads 38, other suitable numbers of threads may also be used, such as one or three.

Figure 1B:
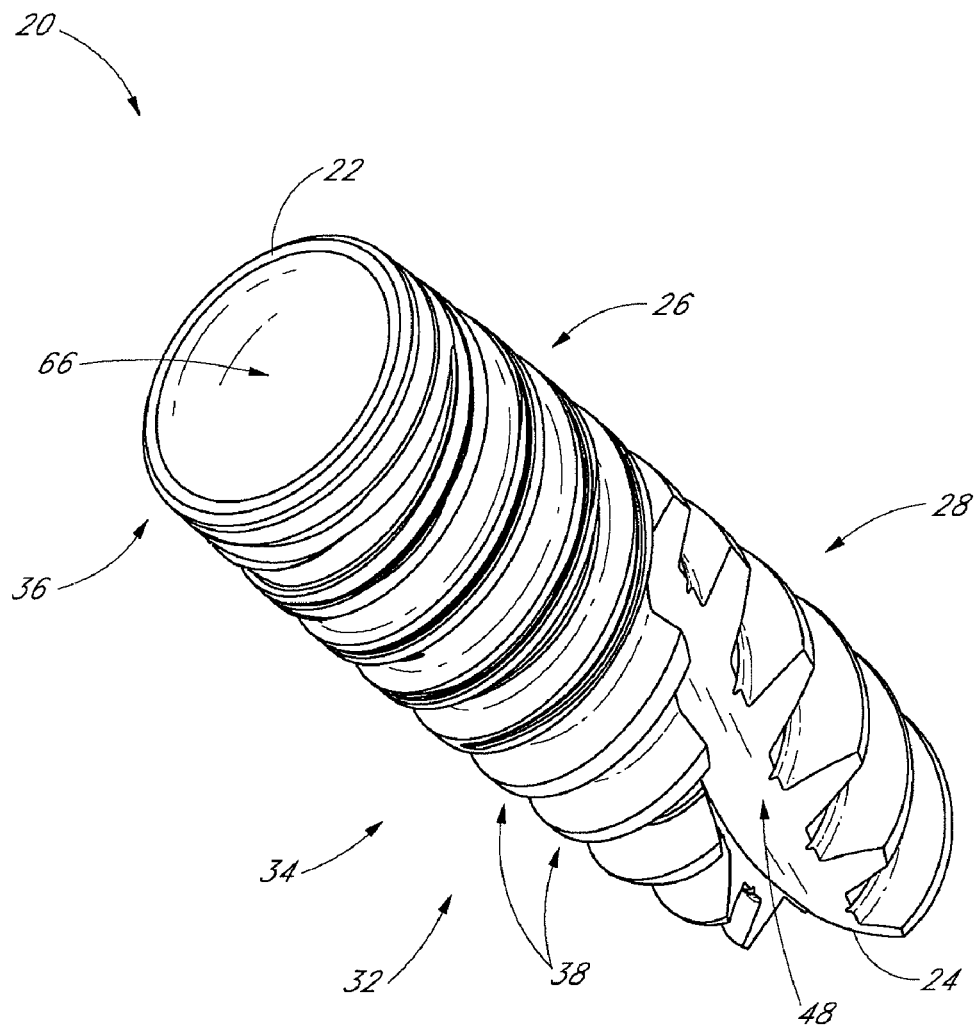
FIG. 1B is a perspective view of the dental implant of FIG. 1A.
Figure 1C:
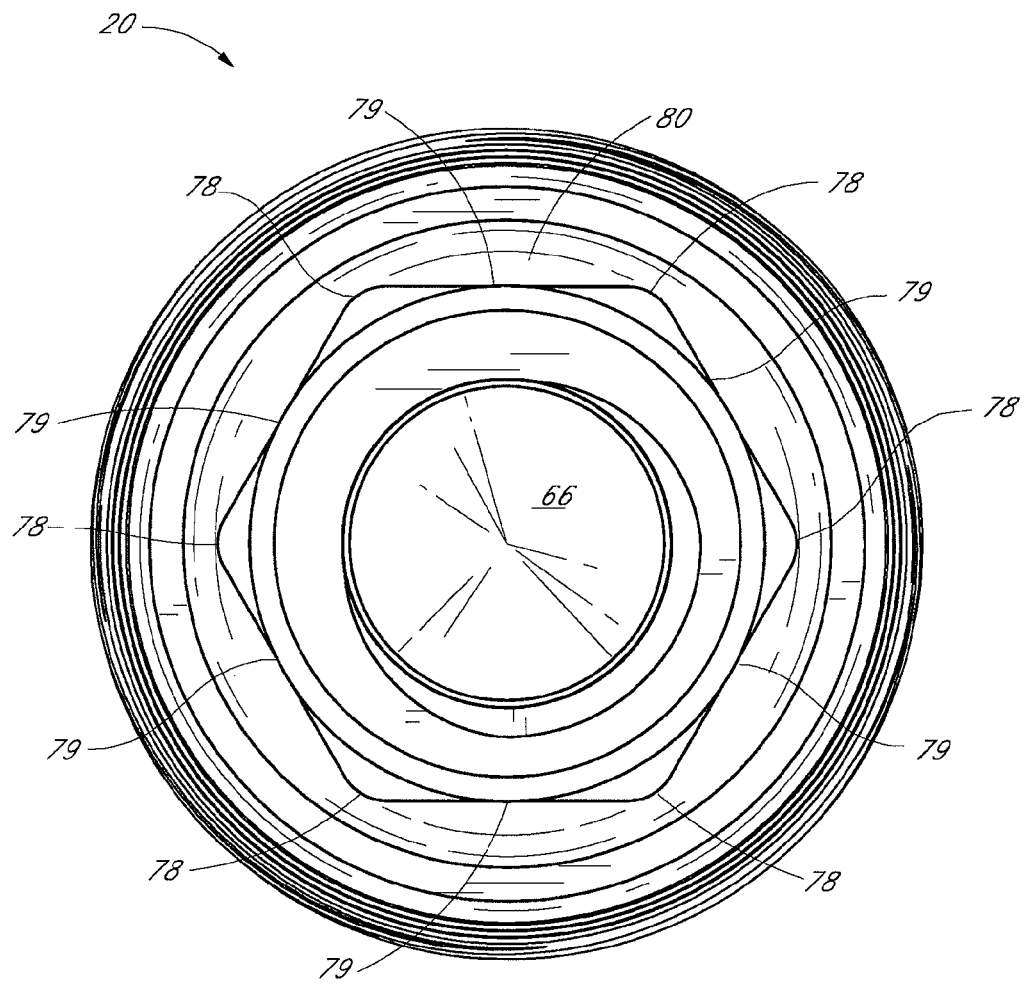
FIG. 1C is a top view of the dental implant of FIG. 1A.
Figure 1D:
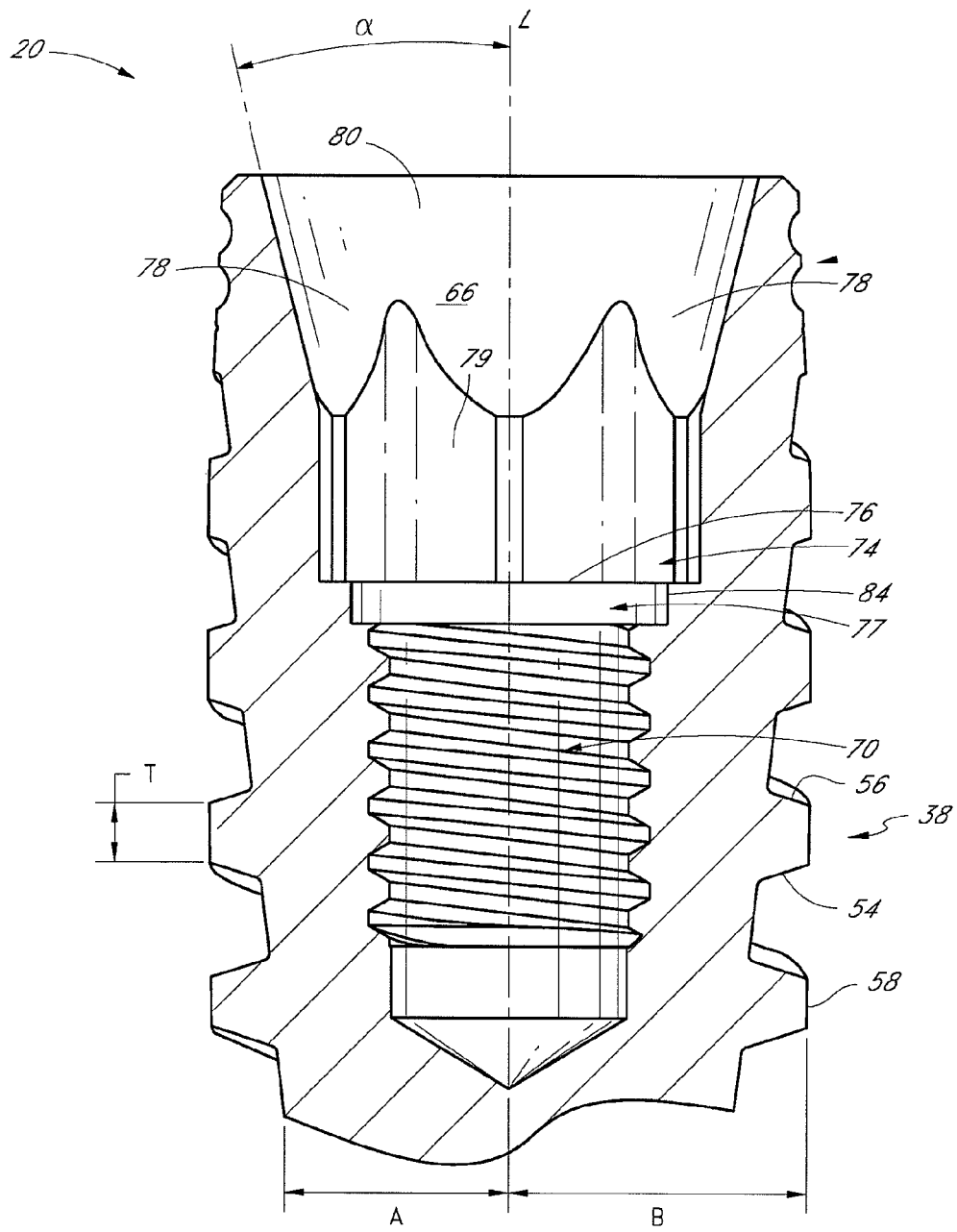
FIG. 1D is a cross sectional side view of the dental implant of FIG. 1A.

As best seen in FIG. 1D, in the illustrated embodiment, the face 58 of each of the threads 38 increases in thickness T as the threads 38 progress from the distal end 24 to the proximal end 22 of the dental implant 20. That is, a distal portion of threads 38 in the distal portion 26 of the implant 20 comprises a thinner face than a proximal portion of the threads 38 on the proximal portion 28 of the implant 20.

The implant body 32 can define at least three different angles: an first angle can be defined by the general shape of the implant body 32; a second angle can be defined by the faces 58 of the threads 38; and a third angle can be defined by the base of the thread. A similar principle can be seen in PCT Application No. PCT/IL2004/000438 (International Publication No. 2004/103202), the entirety of which is incorporated herein by reference. With reference to FIG. 1A and FIG. 1D, the conical shape of the lower portion 34 of the implant body 32 can comprise a variable angle. The variable angle can vary such that the angle at the distal portion 28 is shallower than that at the proximal portion 26. Further, the faces 58 of the threads 38 can also be conical and the faces 58 of the threads 38 can define a varying conical angle. The angle defined by the faces 58 of the threads 38 can be different from the varying conical angle formed by the lower portion 34 of the implant body 32. That is, the conical angle defined by the lower portion 34 of the implant body 32 can be shallower than the conical angle formed by faces 58 of the threads 38. In one embodiment, the conical angle defined by the lower portion 34 of the implant body 32 can be greater than the conical angle formed by faces 58 of the threads 38. Although the illustrated embodiment utilizes the aforementioned conical angle relations, other suitable relations may be used. Such suitable relations may comprise threads 38 in which the faces 58 are not conical and define a generally cylindrical shape and/or where the faces 58 of the threads 38 that define a conical angle that closely matches the conical angle of the lower portion 34 of the implant body 32. In still other embodiments, the angel defined by the faces 58 of the threads 38 and/or the angle defined by the body 32 can be generally parallel to the longitudinal axis of the implant 20 such that they are substantially cylindrical.

With reference to FIG. 1A and FIG. 1B, in the illustrated embodiment, the lower portion 34 of the dental implant 20 comprises two flutes 48 that are positioned on the distal portion 28 of the dental implant 20. The flutes 48 are configured to aid in inserting the dental implant 20 and will be discussed in greater detail below. The lower portion 34 also comprises upper grooves 50 that in the proximal portion 26 of the dental implant 20 are located on the faces 58 of each of the pair of threads. In the distal portion 28 of the implant, lower grooves 52 are located between each of the threads 38 on the surface 35 on the distal portion 28 of the dental implant 20. In general, the grooves 50, 52 extend in a generally helical pattern. In the illustrated embodiment, each groove 50, 52 is substantially continuous. However, in modified embodiments, one or both grooves 50, 52 can be formed to be non-continuous. For example, the grooves 50, 52 can be formed from a series of shorter grooves, dimples, or indentations that together form a generally helical pattern. However, continuous grooves can advantageously promote bone attachment as growth as it has been observed that bone tissue likes to grow along continuous channels.

With reference to FIG. 1A and FIG. 1B, the flutes 48 can comprise a generally helical shape. Further, the flutes 48 can extend from the distal end 24 toward a generally central portion of the dental implant 20. The flutes 48 can be located at generally opposing positions along the lower portion 34 of the implant body 32. In the illustrated embodiment, the flutes 48 are configured to cut, or remove bone, when the dental implant 20 is rotated in a counterclockwise direction. Furthermore, the flutes 48 are configured to allow the dental implant 20 to be rotated clockwise without cutting or removing bone. However, bone removal may be accomplished by rotating the implant counterclockwise.

Although the illustrated embodiment of the dental implant 20 has been shown with flutes 48 that are configured to cut when the dental implant 20 is rotated in a counterclockwise direction, other suitable flutes or flute orientations may also be used. Such suitable flutes or flute orientations may comprise flutes that are configured to cut or provide a tapping function when the dental implant 20 is rotated in a clockwise direction.

With continued reference to FIGS. 1A and 1B the upper grooves 50 and the lower grooves 52 are located on the dental implant 20 to, e.g. provide additional surfaces for osseointegration. The upper grooves 50 can be located on the faces 58 of the portions of the threads 38 located on the proximal portion 26 of the dental implant 20. The upper grooves 50 can begin at the proximal end 22 of the lower portion 34 and extend toward the distal end 24 along the faces 58 of the threads 38 approximately over at least about 37% of the length of the lower portion 34. In the illustrated embodiment, the upper grooves 50 dissipate and/or taper toward the distal end 24 of the implant 20. The dissipation and/or tapering of the upper grooves 50 can occur over a distance approximately within a ¼-½ rotation of the implant 20. In some embodiments, the portion of the faces 58 beyond the dissipation and/or taper will not include the upper grooves 50. The illustrated embodiment of FIG. 1A illustrates that the upper grooves 50 can extend approximately along the proximal 37% of the length of the lower portion 34; however, in other embodiments, the upper grooves 50 can be formed to extend approximately along the proximal 10% to the proximal 80% of the lower portion 34, and in other embodiments the upper grooves 50 may extend approximately along the proximal 20% to the proximal 50% of the lower portion 34.

The lower grooves 52 can begin at the distal end 24 of the dental implant 20 and can be formed between the pair of threads 38 on the outer surface 35 of the lower portion 34 of the implant body 32. The lower grooves 52, in the illustrated embodiment, can extend toward the proximal end 22 of the implant 20 over approximately the distal 75% of the lower portion 34. The outer surface 35 can be formed such that the lower grooves 52 dissipate and/or taper toward the proximal end 22 of the implant 20. The dissipation and/or tapering of the lower grooves 52 can occur over a distance approximately within a ¼-½ rotation of the implant 20. In some embodiments, the portion of the outer surface 35 between the threads beyond the dissipation and/or taper will not include the lower grooves 52. Although the illustrated embodiment shows that lower grooves 52 can extend approximately along the distal 75% of the lower portion 34 of the dental implant 20, in other embodiments, the lower grooves 52 may extend over the distal 10% to the distal 100% of the lower portion 34, and in yet other embodiments may extend over the distal 50% to the distal 80% of the lower portion 34.

In the illustrated embodiment, the configuration of the lower grooves 52 and the upper grooves 50 can result in the upper and lower grooves 50, 52 overlapping along at least a portion of the lower portion 34 of the implant body 32. That is, in the illustrated embodiment, there is a portion of the lower portion 34 of the implant body 32 that comprises both the upper and lower grooves 50, 52. Although the illustrated embodiment shows that the upper grooves 50 and the lower grooves 52 overlap, in other embodiments the upper grooves 50 and the lower grooves 52 may not overlap and/or may terminate at a meeting point between the upper and lower grooves 50, 52 or prior to a meeting point between the upper and lower grooves 50, 52.

The upper and lower grooves 50, 52 can be sized such that the upper and/or lower grooves 50, 52 occupy only a portion of the faces 58 or the outer surface 35 of the lower portion 34 between the threads 38. It will be appreciated that in other embodiments the upper and/or lower grooves 50, 52 may be sized such that they occupy substantially all of the faces 58 and/or substantially all of a portion of the outer surface 35 between the threads 38.

Additionally or alternatively the upper and lower grooves 50, 52 can be formed on the upper and lower flanks 56, 54 of the threads 38.

As best seen in FIGS. 1C and 1D, the dental implant 20 can also comprise a cavity or internal connection interface 66 that is open at the proximal end 22 of the dental implant 20. In the illustrated embodiment, the cavity 66 comprises an conical chamber 68, an hexagonal interlock recess 74 and a threaded chamber 70. The conical chamber 68 and interlock recess 74 can be configured to receive an abutment and the threaded chamber 70 can be configured to receive a coupling screw.

The threaded chamber 70 can be located generally below the abutment chamber 68. As was mentioned above, the threaded chamber 70 can be configured to receive a coupling screw (not shown) that is configured to attach an abutment to the implant 20.

Although the particular embodiment shown in FIGS. 1A-1D has been shown with a conical shaped inner wall 80 and a generally hexagonal shaped interlock recess 74, other suitable shapes and styles of recesses may also be used (e.g., square, non-round, and other shapes). Furthermore, it may be appreciated by one skilled in the art, that some embodiments of the dental implant 20 may omit a cavity 66 all together and may use an external coupling device (e.g., an external hex) and/or an integrally formed abutment, which will be discussed in greater detail with reference to FIGS. 5A and 6A. With respect to the illustrated embodiment, additional details and modified embodiments of the cavity 66 can be found in Applicant's co-pending application filed on the same date as this application under Ser. No. 11/739,024, entitled "DENTAL IMPLANT AND DENTAL COMPONENT CONNECTION," the entirety of which is also incorporated herein by reference.

The illustrated socket 66 is advantageously configured to provide an enhanced connection interface and to provide flexibility such that the implant 20 can mate with multiple types of dental components. In particular, as noted above, the conical portion 68 comprises a side wall that tapers inwardly with respect to the longitudinal axis L of the implant 20 providing a wider initial opening for the socket 66. With reference to FIG. 1C, the particular geometry of the conical chamber 68 defines a conical half angle $\alpha$ with respect to the longitudinal axis L. In one embodiment, the conical half angle is between about 10 degrees and about 20 degrees. That is, the angle between the inner wall 80 and a longitudinal center line L preferably is between about 10 degrees and about 20 degrees. In one embodiment, the conical half angle is about 12 degrees.

In one embodiment, the ratio between the length (d1) of the conical portion 68 and the length (d2) the interlock recess 74 is about 1:1. In one preferred embodiment, the depth (d1) of the conical portion 68 is at least about 1 mm and the depth (d2) of the interlock recess 74 is at least about 1 mm. As shown in FIG. 1D, the length (d1) of the conical portion 68 is a distance measured in a vertical direction from the top surface 21 of the implant 20 to the portion of the socket 66 in which the tapered surfaces 80 of the conical portion 68 terminate. The length (d2) of the interlock recess 74 is measured in a vertical direction from the end of the conical portion 68 to the end of the interlock recess 74. The ratios and length of the conical portion 68 and the depth and length of the interlock recess 74 advantageously combine the benefits of a sufficiently long tapered connection to provide an effective seal with a sufficiently long interlock recess 74 such that a sufficient driving torque can be transmitted to the implant 20, when the implant is driven into the patient.

Yet another advantage of the illustrated embodiment is an area or thickness of the substantially planar top surface 21 of the implant 20. In one embodiment, the top surface 21 of the implant 20 advantageously can provide a surface to support certain dental restorations on the top surface 21 of the implant 20. Additionally or alternatively, the top surface 21 can be used to support a component that bypasses the interlock recess 74. Accordingly, in one embodiment, the top surface 21 of the implant 20 has at least a thickness as measured between the outer and inner periphery of the top surface 21 that is greater than at least 0.2 mm and in another embodiment greater than about 0.25 mm. In one embodiment, the thickness of the top surface 21 is about 0.25 mm.

The embodiments described above provide for improved stability of a dental implant when implanted in the alveolar bone. Furthermore, certain embodiments of the invention provide efficient utilization of space. For example, as described above, in certain embodiments, the upper groove 50 is located on the face 58 of the thread 38 at a portion of the body 32 containing the internal connection interface 66. Hence, the strength of the body of the implant 20 at this location remains unaffected. If the upper groove 50 had been located on the body 32 at this portion, less space would have been available for the internal connection interface 66 with maintained minimum wall thickness at specific dimensions to maintain body strength. Hence, having the upper groove 50 positioned at the face 58 in the portion of the internal connection interface 66 improves the space available for the connection interface 66 and still provides for improved stability of the implant 20. In some embodiments, the wall thickness will be sufficient if the upper groove 50 is located at the face 58 only at the portion of the interlock recess 74 but at least partly not at the location of he threaded chamber 70.

In the portion of the body 32 that does not include the internal connection interface 66, the lower groove 52 can be located on the body 32. This will not deteriorate the strength of the implant 20 substantially as the implant 20 of the illustrated embodiment does not include any internal recess 66 at this portion. This provides for the option of having a thinner face of the thread 38 at this location, such as a variable thread thickness, which may provide for even further improved stability of the implant 20. Hence, the location of the grooves 50, 52 provides for stability themselves as well as their specific locations. In addition, efficient utilization of the space available without compromising strength is provided. The locations also provides for flexibility, as the locations for the grooves 50, 52 can be used on implants having either an internal connection interface 66 or an external connection interface (described below).

Figure 2A:
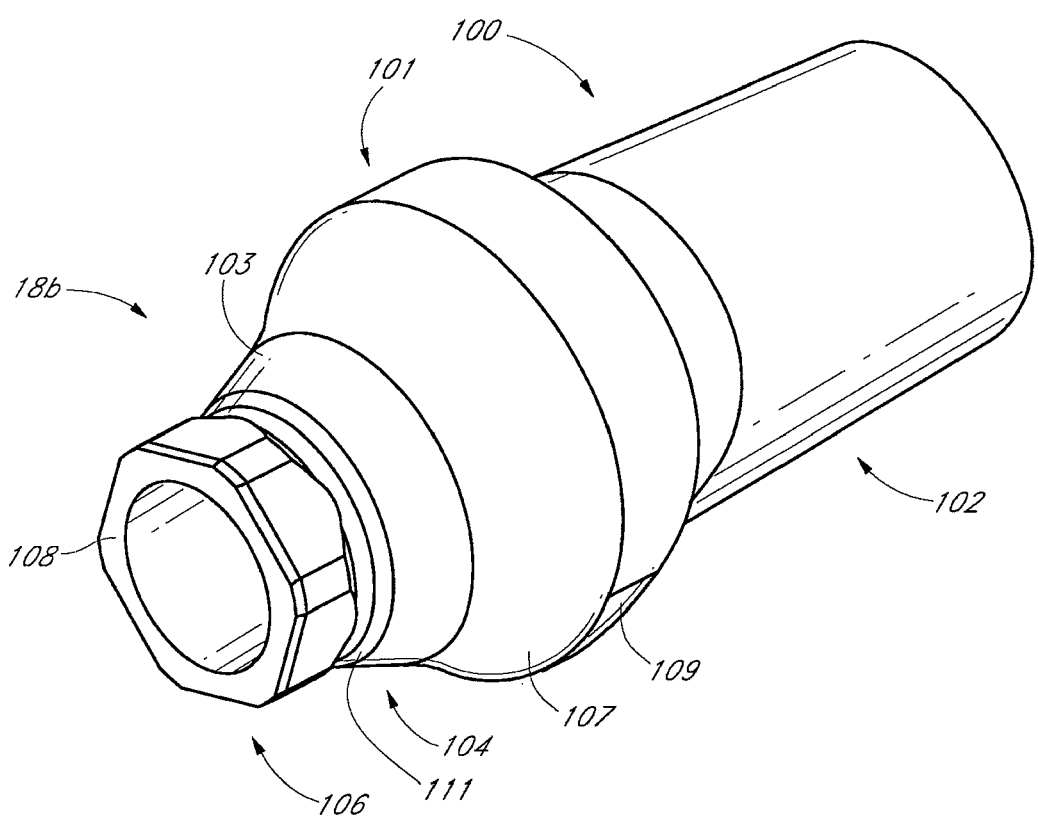
FIG. 2A is perspective view of an embodiment of an abutment, which is configured to mate with the implant of FIG. 1A.
Figure 2B:
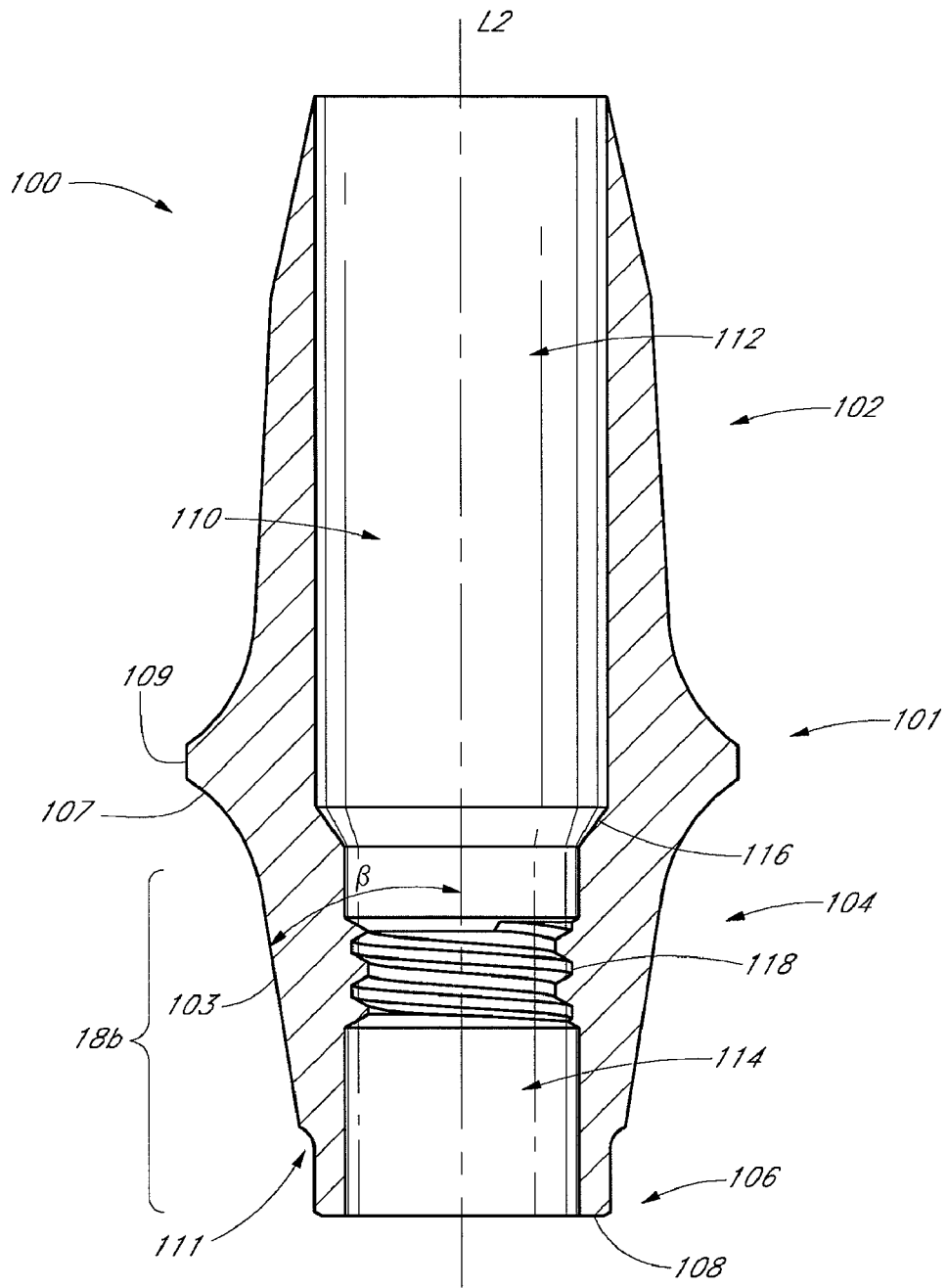
FIG. 2B is a cross sectional side view of the abutment of FIG. 2A

FIGS. 2A and 2B illustrate an embodiment of an abutment 100 that is configured to mate with the implant 20 described above. As will be explained below, the abutment 100 is one example of a variety of dental components, such as, for example, a healing cap, impression coping, a temporary healing abutment, or a final abutment that can be configured to be attached to the implant 20. Additional details regarding the illustrated embodiment and regarding modified embodiments of the abutment 100 and other mating components can be found in Applicant's co-pending application filed on the same date as this application Ser. No. 11/739,024, entitled "DENTAL IMPLANT AND DENTAL COMPONENT CONNECTION," the entirety of which is incorporated herein by reference. The abutment 100 can be made of a dental grade titanium, however, other suitable materials such as various types of ceramics can be used.

As seen in FIGS. 2A and 2B the abutment 100 can include a shaped portion 102, a conical portion 104, and an interlock portion 106. The interlock portion 106 comprises a generally hexagonal shape that is sized to fit with in the interlock recess 74 of the dental implant 20. Although the particular embodiment of the abutment 100 has been illustrated with a generally hexagonal interlock portion 106 other suitable shapes may also be used. Such alternative suitable shapes may comprise other shapes configured to mate with interlock recess 74 and to prevent rotation of the abutment 100.

With continued reference to FIGS. 2A and 2B, the conical portion 104 is configured to be at least partially inserted into the abutment chamber 68 and/or to rest on top of the corners 78 of the dental implant 20. Above the conical portion 104, the abutment 100 comprises the shaped portion 102, which in the illustrated embodiment is shaped such that the abutment 100 is a final abutment. It should be appreciated that the shaped portion 102 can be shaped into any desirable shape such as that of a temporary abutment, healing abutment etc. As described in the afore-mentioned Applicant's co-pending application, the conical portion 104 of the abutment 100 can engage the top surface of the implant in a tapered or sealed fit.

As best seen in FIG. 2B, an inner bore 110 can extend through the center of the abutment 100. The inner bore 110 can be divided into a first and second region 112 and 114. The first region 112 can comprise a diameter that is slightly larger than the diameter of the second region 114. Accordingly, a seat 116 can be formed between the first and second regions 112 and 114. This seat 116 can support a coupling member 200 (see FIG. 3A), which will be described below. The second region 114 can include internal capture threads 118 that are configured to interface with the coupling member 200.

FIGS. 3A and 3B illustrate an embodiment of a coupling member 200 that can be used mechanically couple the abutment 100 to the implant 20. The coupling member 200 can also be made of a dental grade titanium alloy, although other suitable materials can be used. The coupling member 200 can be sized and shaped to extend through the inner bore 110 of the abutment 100 and into the cavity 66 of the implant 20. The coupling member 200 can include an externally threaded lower region 202 that engages the internal capture threads 118 of the abutment 100 and engages the threaded chamber 70 of the implant 20. The threads 204 of the coupling member 200 can engage the capture threads 118 so that the coupling screw 200 does not become disassociated as the abutment 100 is transferred and lifted into a patient's mouth.

The coupling member or screw 200 also includes a recess 206 in a shape configured to receive a Unigrip® rotational tool provided by Nobel Biocare™. In other embodiments, the recess 208 can have a different shape, such as, for example, a hexagon configured to allow for the insertion of a hexagonally shaped tool such as a conventional Allen® wrench to install or remove the coupling screw 200 from the implant 20.

Figure 4:
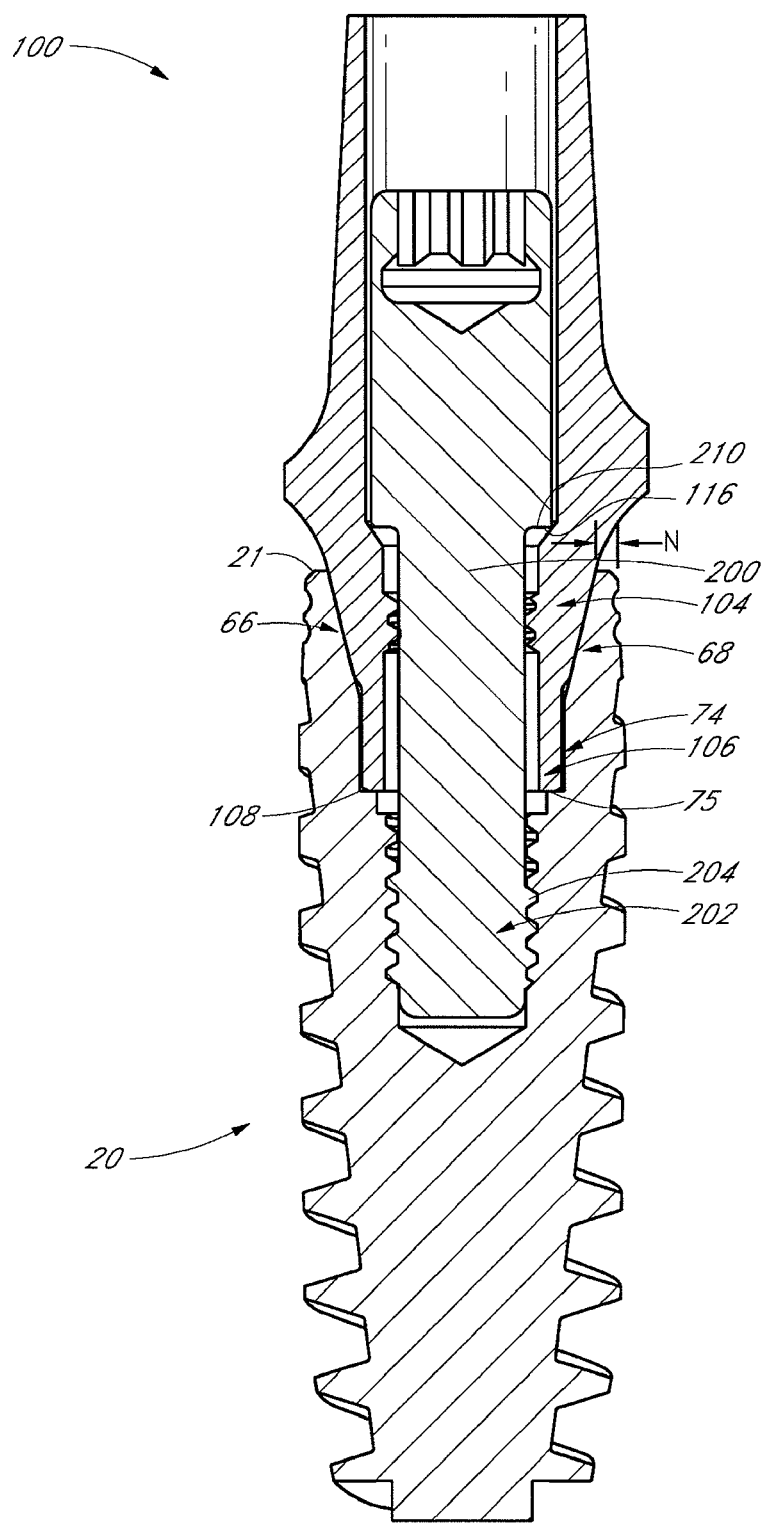
FIG. 4 is a cross sectional side view of the implant of FIG. 1A and the abutment of FIG. 2A attached together with the coupling bolt of FIG. 3A.

FIG. 4 is a side cross sectional view illustrating the abutment 100 coupled to the dental implant 20 with the coupling screw 200. As illustrated, the interlock portion 106 of the abutment 100 is aligned and inserted into the interlock recess 74 of the dental implant 20. Furthermore, the conical portion 104 of the abutment 100 is inserted into the receiving chamber 68 of the dental implant 20. The abutment 100 can be inserted into the cavity 66 of the dental implant 20 such that the lower end 108 of the interlock portion 106 is in contact with the lower end 75 of the interlock recess 74. As shown in FIG. 4, a top surface 21 of the implant 20 can remain exposed when the abutment 100 is coupled to the implant 20. In one embodiment, the exposed top surface has thickness N of at least about 0.2 millimeters and in one embodiment a thickness of about 0.25 millimeters.

With continued reference to FIG. 4, the lower threaded region 202 of the coupling screw 200 can be engaged with the threaded chamber 70 of the dental implant 20 and the seat 210 of the coupling screw 200 is abutting the seat 116 of the abutment 100. This engagement of the coupling screw 200 and the abutment 100 and the dental implant 20 can thereby secure the abutment 100 to the dental implant 20.

Although the embodiment of the dental implant 20 described above has been shown with a cavity 66 for receiving a separate abutment 100, other configurations may also be used. Such an alternate or modified configuration is illustrated in FIG. 5A.

Figure 5:
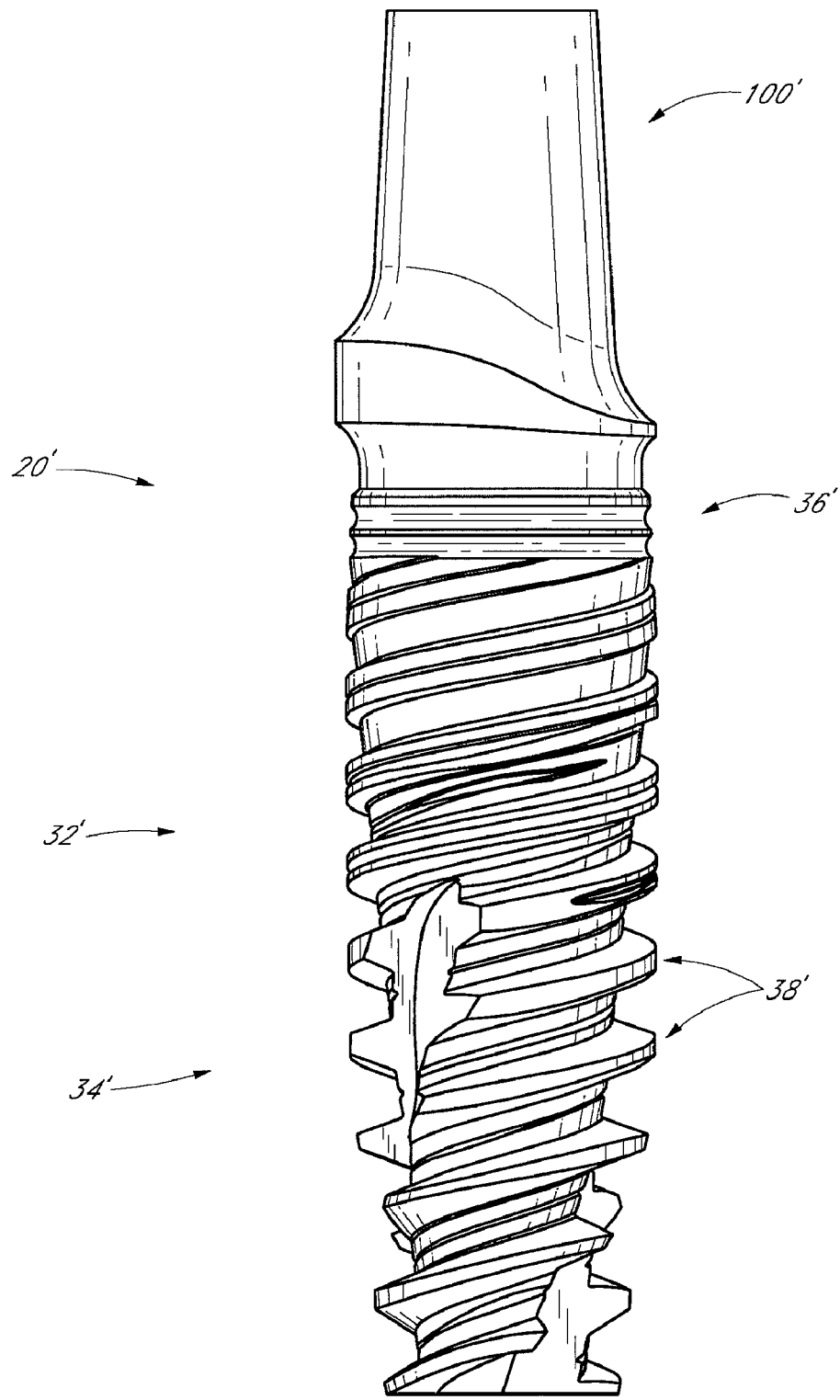
FIG. 5 is a side view of another embodiment of the dental implant.

The dental implant 20', shown in FIG. 5, can comprise the same general shapes and structures as the dental implant 20 described above. The dental implant 20' includes an implant body 32' that comprises a collar 36' and a lower portion 34' that further comprises threads 38'. One difference between the embodiment of the implant 20' and the embodiment of the dental implant 20 is that the dental implant 20' comprises an integrated abutment 100' that is integrally formed with the implant body 32' such that the abutment 100' and the implant body 32' are one continuous piece.

Similar to the abutment 100 of FIG. 2A, the integrally formed abutment 100' can be formed into any suitable shape such as that of a healing cap, impression coping, a temporary healing abutment, or a final abutment. As with the abutment 100 and the implant 20, the implant 20' is made of titanium, however, other suitable materials such as various types of ceramics can also be used.

Figure 6:
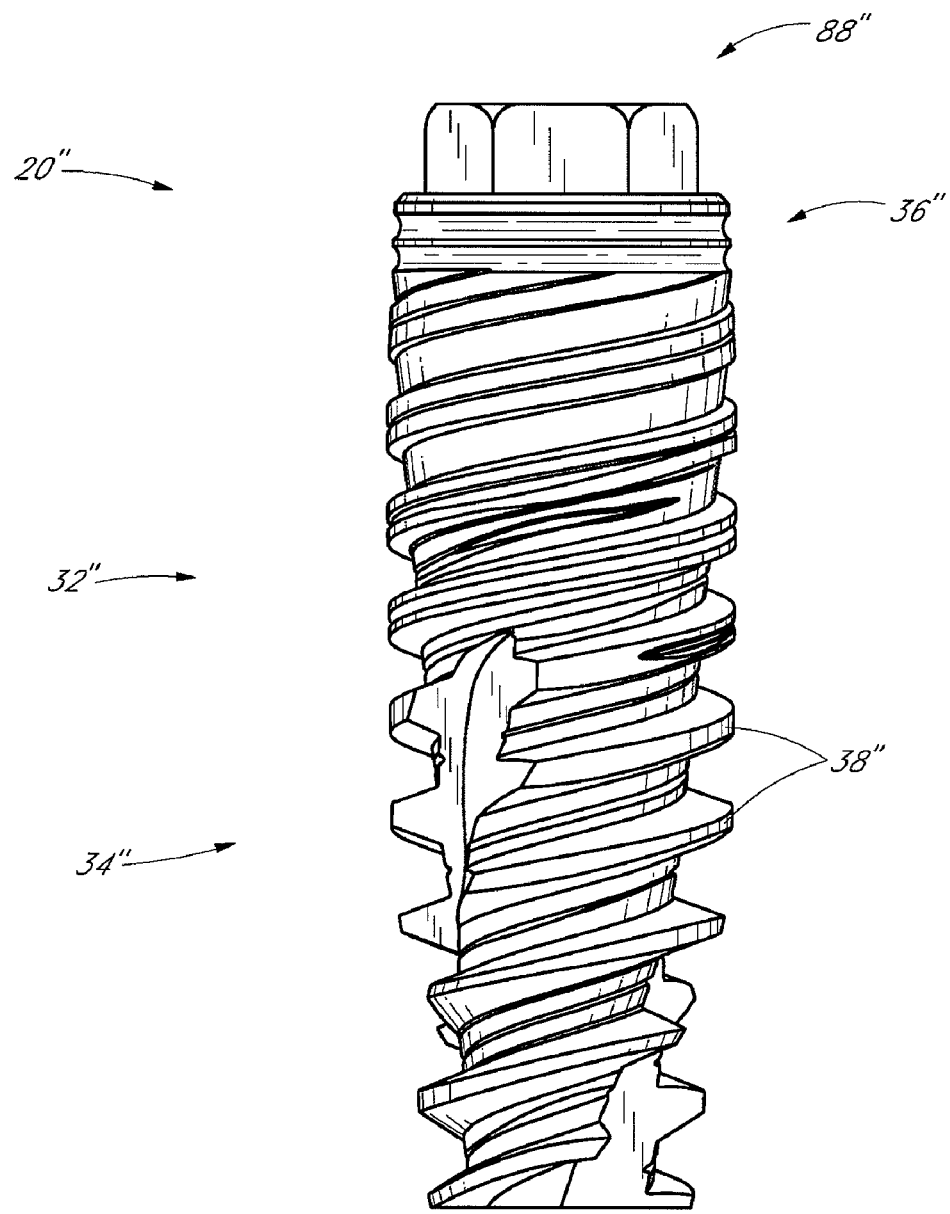
FIG. 6 is a side view of yet another embodiment of the dental implant.
Figure 7:
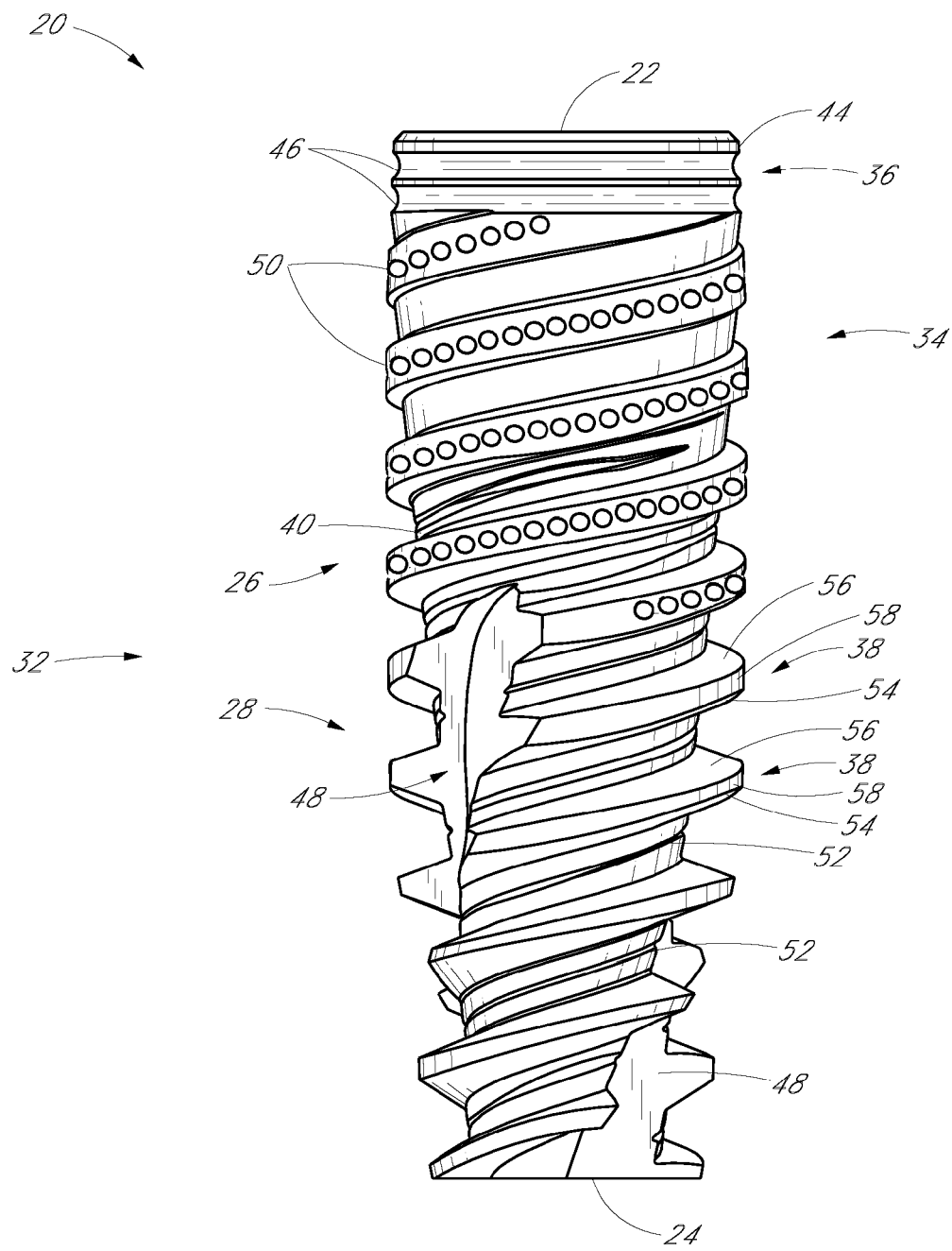
FIG. 7 is a side view of another embodiment of the dental implant.

Another alternative embodiment of a dental implant is shown in FIG. 6. The dental implant 20", once again, can comprise the same general shapes and structures as that of the dental implant 20. The dental implant 20" comprises an implant body 32" that comprises a collar 36" and a lower portion 34". Threads 38" are located in the lower portion 34". One difference between the embodiment of the implant 20" and the embodiment of the dental implant 20' or the embodiment of the dental implant 20 is that the dental implant 20" comprises a hexagonal structure 88" that extends above the collar 36" and is integrally formed with the implant 20". The hexagonal structure 88" is configured to mate with a variety of different devices including implant insertion tools or various types of abutments. Such suitable abutments for mating with the dental implant 20" could comprise a suitable recess to receive the hexagonal structure 88", however other suitable connection methods may be used to attach an abutment to the dental implant 20".

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while the number of variations of the invention have been shown and described in detail, other modifications, which are within the scope of this invention, will be readily apparent to those of skill in the art based upon this disclosure.

It is also contemplated that various combinations or subcombinations of the specific features and aspects of the embodiments may be made and still fall within the scope of the invention. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A dental implant for supporting a dental prosthesis, the implant comprising:
    a body comprising an outer surface, a distal end, and a proximal end that forms a top surface of the dental implant;
    an internal connection socket formed in the body with an opening on the top surface of the dental implant and a thread chamber positioned below the internal connection socket;
    at least one thread located on at least a threaded portion of the outer surface of the body, the thread comprising a proximal flank and a distal flank, the thread further comprising a face extending between the proximal flank and the distal flank, the threaded portion having a thread length extending between a proximal end of the threaded portion and a distal end of the threaded portion, the threaded portion starting above a distal end of the internal connection socket;
    a first groove having a helical pattern, the first groove being formed on at least a portion of the face of the thread, the first groove extending from the proximal end of the threaded portion over at least a proximal 20% to at most a proximal 50% of the length of the threaded portion; and
    a second groove having a helical pattern, the second groove being formed on at least a portion of the body, the second groove beginning below at least a proximal 20% of the length of the threaded portion with no groove on the body over the proximal 20% of the threaded portion.

2. The dental implant of claim 1 wherein the first groove is continuous.

3. The dental implant of claim 1 wherein the first groove is formed as a series of dimples.

4. The dental implant of claim 1 wherein the second groove is continuous.

5. The dental implant of claim 1 wherein the body further comprises a collar located above the threaded portion of the outer surface.

6. The dental implant of claim 5 wherein the second helical groove extends over a distal 10% to a distal 80% of the threaded portion.

7. The dental implant of claim 5 wherein the second helical groove extends over a distal 50% to a distal 80% of the threaded portion.

8. The dental implant of claim 1 wherein at least a portion of the body comprises both the first helical groove and the second helical groove.

9. The dental implant of claim 1 wherein substantially all of the body comprises only one of the first helical groove and the second helical groove.

10. The dental implant of claim 1 wherein the dental implant further comprises at least one flute located on the implant.

11. The dental implant of claim 1 wherein the collar comprises at least one circumferential groove located on an outer surface of the collar.

12. The dental implant of claim 1, wherein the face increases in thickness from a distal thread portion to a proximal thread portion.

13. The dental implant of claim 12 wherein the face defines a first conical angle and the body defines a second conical angle, the first conical angle being different from the second conical angle.

14. The dental implant of claim 13 wherein the second conical angle is shallower than the first conical angle.

15. The dental implant of claim 12 wherein the dental implant further comprises at least one flute located on the implant.

16. The dental implant of claim 15 wherein the flute is configured to cut when the dental implant is rotated in one of a clockwise direction and a counterclockwise direction.

17. The dental implant of claim 1, wherein the internal connection socket includes at least one surface extending from the top surface that tapers inwardly towards a longitudinal axis of the implant to form a substantially conical portion.

18. The dental implant of claim 17, wherein the internal connection socket further comprises an interlock recess that includes at least one anti-rotational feature positioned below the substantially conical portion.

\* \* \* \* \*